US011169146B2

(12) United States Patent
Boenitz-Dulat et al.

(10) Patent No.: US 11,169,146 B2
(45) Date of Patent: *Nov. 9, 2021

(54) ACTIVITY ASSAY FOR BOND FORMING ENZYMES

(71) Applicant: Hoffmann-La Roche Inc., Little Falls, NJ (US)

(72) Inventors: Mara Boenitz-Dulat, Tutzing (DE); Erhard Kopetzki, Penzberg (DE); Peter Kratzsch, Penzberg (DE); Martin Schatte, Karlsbad (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 118 days.

This patent is subject to a terminal disclaimer.

(21) Appl. No.: 15/625,950

(22) Filed: Jun. 16, 2017

(65) Prior Publication Data

US 2017/0370913 A1 Dec. 28, 2017

Related U.S. Application Data

(63) Continuation of application No. PCT/EP2015/079615, filed on Dec. 14, 2015.

(30) Foreign Application Priority Data

Dec. 17, 2014 (EP) .................................... 14198535

(51) Int. Cl.
*G01N 33/53* (2006.01)
*C12Q 1/37* (2006.01)
*C12Q 1/00* (2006.01)
*A61K 38/00* (2006.01)

(52) U.S. Cl.
CPC ......... *G01N 33/5302* (2013.01); *C12Q 1/005* (2013.01); *C12Q 1/37* (2013.01); *A61K 38/00* (2013.01); *G01N 2333/90* (2013.01); *G01N 2333/96413* (2013.01)

(58) Field of Classification Search
CPC ..... G01N 33/5302; G01N 2333/96413; G01N 2333/90; C12Q 1/37; C12Q 1/005; A61K 38/00
See application file for complete search history.

(56) References Cited

U.S. PATENT DOCUMENTS

| 8,247,198 | B2 | 8/2012 | Gorke et al. |
| 10,864,277 | B2 | 12/2020 | Grawunder et al. |
| 2009/0117628 | A1 | 5/2009 | Gorke et al. |
| 2014/0030697 | A1 | 1/2014 | Ploegh et al. |
| 2014/0057317 | A1* | 2/2014 | Liu .......................... C12N 9/52 435/68.1 |
| 2015/0152134 | A1 | 6/2015 | Pentelute et al. |
| 2016/0082046 | A1 | 3/2016 | Lodish et al. |
| 2016/0193355 | A1 | 7/2016 | Qin et al. |

FOREIGN PATENT DOCUMENTS

| WO | 02/059142 | 1/2002 |
| WO | 2007/140371 A2 | 6/2007 |
| WO | 2010/099536 A2 | 2/2010 |
| WO | 2010/099536 A3 | 2/2010 |
| WO | 2010/087994 A2 | 5/2010 |
| WO | 2012/145522 | 10/2012 |
| WO | 2013/016653 A1 | 1/2013 |
| WO | 2013/003555 A1 | 3/2013 |
| WO | 2013/1533203 | 10/2013 |
| WO | 2013/177231 | 11/2013 |
| WO | 2014/001325 A1 | 1/2014 |
| WO | 2014/001324 A1 | 3/2014 |
| WO | 2014/055936 | 4/2014 |
| WO | 2014/177042 | 6/2014 |
| WO | 2014/131906 A1 | 9/2014 |
| WO | 2014/145441 | 9/2014 |
| WO | 2014/183066 A2 | 11/2014 |

OTHER PUBLICATIONS

Clancy et al. Sortase Transpeptidases: Insights into Mechanism, Substrate Specificity and Inhibition. Biopolymers. 2010 ; 94(4): 385-396 (Year: 2010).*

Frankel et al., "*Staphylococcus aureus* Sortase Transpeptidase SrtA: Insight into the Kinetic Mechanism and Evidence for a Reverse Protonation Catalytic Mechanism" Biochemistry 44(33):11188-11200 (2005).

Heck et al., "Continuous Monitoring of Enzymatic Reactions on Surfaces by Real-Time Flow Cytometry: Sortase A Catalyzed Protein Immobilization as a Case Study" Bioconjugate Chemistry 25(8):1492-1500 (2014).

International Search Report of PCT/EP2015/079615 dated Mar. 14, 2016.

Matsumoto et al., "Site-Specific Tetrameric Streptavidin-Protein Conjugation using Sortase A" Journal of Biotechnology 152:37-42 (2011).

Matsumoto et al., "Sortase A-Catalyzed Site-Specific Coimmobilization on Microparticles via Streptavidin" Langmuir 28(7):3553-3557 (2012).

Li et al., "A novel reporter system monitoring Sortase A catalyzed protein ligation efficiency" Chinese Journal of Biotechnology 30(2):284-293 ( 2014).

(Continued)

*Primary Examiner* — Taeyoon Kim
(74) *Attorney, Agent, or Firm* — Nicole Fortune

(57) ABSTRACT

Herein is reported a method for the detection of a sortase in a sample, comprising the following steps:

a) incubating the sample with a first substrate comprising an immobilization tag and a second substrate comprising a detectable label, whereby in the presence of a sortase in the sample a conjugate comprising the immobilization tag and the detectable label is formed, b) immobilizing the conjugate of step a) via/using the immobilization tag to a solid phase, c) detecting the immobilized conjugate via/using the detectable label and thereby detecting the sortase in the sample.

32 Claims, 4 Drawing Sheets

Specification includes a Sequence Listing.

(56) References Cited

OTHER PUBLICATIONS

Oteng-Pabi et al., "Continous enzyme-coupled assay for microbial transglutaminase activity" Analytical Biochemistry 441(2):169-173 (2013).
Ton-That et al., "Anchoring of surface proteins to the cell wall of *Staphylococcus aureus* Sortase catalyzed in vitro transpeptidation reaction using LPXTG peptide and NH(2)-Gly(3) substrates" The Journal of biological chemistry 275(13):9876-81 ( 2000).
Ton-That et al., "Purification and Characterization of Sortase, the Transpeptidase that Cleaves Surface Proteins of *Staphylococcus aureus* at the LPXTG Motif" PNAS 96(22):12424-12429 (Oct. 26, 1999).
Antos et al., "Site-Specific N- and C-Terminal Labeling of a Single Polypeptide Using Sortases of Different Specificity" Journal of the American Chemical Society 131:10800-10801 ( 2009).
Biswas et al., "Sorting of LPXTG Peptides by Archetypal Sortase A: Role of Invariant Substrate Residues in Modulating the Enzyme Dynamics and Conformational Signature of a Productive Substrate" Biochemistry 53(15):2515-2524 ( 2014).
Branden et al. Introduction to Protein Structure "Prediction, Engineering, and Design of Protein Structures" New York:Garland Publishing Inc.,:247 ( 1991).
Clancy et al., "Sortase transpeptidases: Insights into mechanism, substrate specificity, and inhibition" Biopolymers 94(4):385-396 ( 2010).
Hess et al., "M13 Bacteriophage Display Framework that Allows Sortase-Mediated Modification of Surface-Accessible Phage Proteins" Bioconjugate Chemistry 23:1478-1487 ( 2012).
International Search Report for PCT/EP2015/079692 dated Mar. 16, 2016.
Levary et al., "Protein-Protein Fusion Catalyzed by Sortase A" PLoS ONE 6(4 SUPPL e18342):1-6 ( 2011).
Li et al., "Irreversible Site-Specific Hydrazinolysis of Proteins by Use of Sortase" Angewandte Chemie International Edition in English 53:2198-2202 ( 2014).
Madej et al., "Engineering of an Anti-Epidermal Growth Factor Receptor Antibody to Single Chain format and Labeling by Sortase A-Mediated Protein Ligation" Biotechnology and Bioengineering 109(6):1461-1470 ( 2012).
Marraffini et al., "Anchoring of Surface Proteins to the Cell Wall of *Staphylococcus aureus*" Journal of Biological Chemistry 279(36):37763-37770 (Sep. 3, 2004).
Marraffini et al., "Sortases and the Art of Anchoring Proteins to the Envelopes of Gram-Positive Bacteria" Microbiology and Molecular Biology Reviews 70:192-221 ( 2006).
Marvin et al., "Recombinant approaches to IgG-like bispecific antibodies" Acta Pharmacologica Sinica 26(6):649-658 (Jun. 2005).
Meissner, P. et al. et al., "Transient gene expression: recombinant protein production with suspension-adapted HEK293-EBNA cells" Biotechnol Bioeng 75:197-203 ( 2001).
Popp et al., "Making and Breaking Peptide Bonds: Protein Engineering Using Sortase" Angew. Chem. Int. Ed. 50:5024-5032 ( 2011).
Popp et al., "Sortase-catalyzed transformations that improve the properties of cytokines" PNAS 108:3169-3174 ( 2011).
Race et al., "Crystal Structure of *Streptococcus pyogenes* Sortase A Implications for Sortase Mechanism" Journal of Biological Chemistry 284:6924-6933 ( 2009).
Sadowski et al., "The sequence-structure relationship and protein function predicition" Current Opinion in Structural Biology 19:357-362 ( 2009).
Seffernick, J. et al., "Melamine Deaminase and Atrazine Chlorohydrolase: 98 Percent Identical but Functionally Different" Journal of Bacteriology 183(8):2405-2410 ( 2001).
Strijbis, K. et al., "Protein Ligation in Living Cells Using Sortase" Traffic 13:780-789 ( 2012).
Ta et al., "Enzymatic Single-Chain Antibody Tagging A Universal Approach to Targeted Molecular Imaging and Cell Homing in Cardiovascular Disease" Circulation Research 109:365-373 ( 2011).

Tang et al., "Identification of Dehalobacter reductive dehalogenases that catalyse dechlorination of chloroform, 1,1,1-trichloroethane and 1,1-dichloroethane" Philosophical Transactions of The Royal Society B 368:1-10 ( 2013).
Tsukiji et al., "Sortase-Mediated Ligation: A Gift from Gram-Positive Bacteria to Protein Engineering" ChemBioChem 10:787-798 ( 2009).
Witkiowski, A. et al., "Conversion of a â-Ketoacyl Synthase to Malonyl Decarboxylase by Replacement of the Active-Site Cysteine with Glutamine" Biochemistry 38:11643-11650 ( 1999).
Yamamura et al., "Enhancement of Sortase A-Mediated Protein Ligation by Inducing a beta-Hairpin Structure around the Ligation Site" Chem. Commun. 47:4742-4744 ( 2011).
Ton-That et al., "Anchoring of Surface Proteins to the Cell Wall of *Staphylococcus aureus*" Journal of Biological Chemistry 277(9):7447-7452 ( 2002).
NCBI Database, 002984641.1, (sortase SrtA [*Streptococcus pyogenes*]), pp. PN 171203 May 2013.
NCBI Database, 031862293.1, (sortase A [*Staphyloccus aureus*]), pp. PN 171203 Sep. 2014.
Tan et al., "Applications of Transpeptidase Sortase A for Protein Modifications" Progress in Chemistry 26(10):1741-1751 (2014).
Walsh, Christopher Antibiotics: actions, origins, resistance Washington, D.C.:ASM Press, (2003).
Abbot, A., et al., "Processing of Leather Using Deep Eutectic Solvents"ACS Sustainable Chem Eng 3(6):1241-1247 (Apr. 20, 2015).
Antos, John M., et al. "Supporting Information" Title: Site-specific N- and C-terminal labeling of a single polypeptide using sortases of different specificity, Whitehead Institute for Biomedical Research, 9 Cambridge Center, Cambridge, MA 02142, pp. S1-S20 (2009).
Clancy et al., "Sortase Transpeptidases: Insights into mechanism, substrate specificity and inhibition" Peptide Science 94(4):385-396 (2010).
Dai, Y et al. Natural Deep Eutectic Solvents and Their Application in Natural Product Research and Development, Dissertation "3"Universiteit Leiden, (Sep. 24, 2013).
Durand et al., "Deep eutectic solvents: Synthesis, application, and focus on lipase-catalyzed reactions" Eur. J. Lipid Sci. Technol. 115:379-385 ( 2013).
Garandeau et al., "The Sortase SrtA of Listeria monocytogenes Is Involved in Processing of Inernalin and in Virulence" Infection and Immunity: 1382-1390 (Mar. 2002).
Garcia et al., "Deep Eutectic Solvents: Physiochemical Properties and Gas Separation Application" Energy & Fuels 29:2616-2644 (2015).
Gaspar, A., et al., "Baccillus anthracis Sortase A (SrtA) Anchors LPXTG Motif-Containing Surface Proteins to the Cell Wall Envelope" J Bacterol 187(13):4646-4655 (Jul. 1, 2005).
Guimaraes et al., "Site-specific C-terminal and internal loop labeling of proteins using sortase-mediated reactions" Nature Protocols 8:1787-1799 (2013).
Hongyuan et al., "Sortase-Mediated Protein Ligation: A New Method for Protein Engineering" J. Am. Chem. Soc. 126:2670-2671 ( 2004).
Huang et al., "Deep eutectic solvents can be viable enzyme activators and stabilizers" Journal of Chem. Technol Biotechnol 89:1875-1981 ( 2014).
ISR and Written Opinion of PCT/EP2016/072512 (dated Nov. 17, 2016).
ISR for PCT/EP2016/072502 (Nov. 8, 2016).
ISR for PCT/EP2017/052318 (May 4, 2017).
ISR of PCT/EP2016/072510 (Nov. 15, 2016).
Kyoui et al., "Genetic distance in the whole-genome perspective on Listeria monocytogenes strains F2-382 and NIHS-28 that show similar subtyping result" BMC Microbiology 14:309 ( 2014).
Lindberg et al., "Deep eutectic solvents (DESs) are viable cosolvents for enzyme-catalyzed epoxide hydrolysis" Journal of Biotechnology 147:169-171 ( 2010).
Ling, J., et al., "Protein Thioester Synthesis Enabled by Sortase"J Am Chem Soc 134(26):10749-10752 (Jun. 11, 2012).
Maugeri et al., "Chymotryspin-Catalyzed Peptide Synthesis in Deep Eutectic Solvents" European Journal of Organic Chemistry:4223-4228 ( 2013).

(56) References Cited

OTHER PUBLICATIONS

Nguyen et al., "Establishment of an experimental system allowing immobilization of proteins on the surface of Bacillus subtilis cells" Journal of Biotechnology 122:473-482 (2006).
Other Database, Database EBI accession No. UNIPROT:AOAOE1R5I2, (SubName: Full=Putative cysteine portease ywpE {ECO:0000313|EMBL:CCO63533.1}; EC=3.4.22.—{ECO:0000313|EMBL:CCO63533.1};) May 27, 2015.
Other Database, UNIPROT:A0A0B8RCN4, Database accession no. UNIPROT:A0A0B8RCN4 SubName: Full=Cysteine portease {ECO:0000313:EMBL:GAM94542.1}; SubName: Full=Sortase {ECO:00003131EMBL:AGR15336.1}; SubName: Full=Sortase A {ECO:0000313;EMBL:AKK25356.1} Sep. 16, 2015.
Other Database, UNIPROT:A9LY59, retrieved from EBI accession No. UNIPROT:A9LY59, SubName: Full=Sortase A {ECO:0000313:EMBL:ABX11549.1}; Flags: Fragement; Feb. 5, 2008.
Schmohl, L. et al., "Sortase-mediated ligations for the site-specific modification of proteins" Curr Opin Chem Biol 22:122-128 (Oct. 1, 2014).
Smith, E., et al., "Deep Eutectic Solvents (DESs) and Their Applications" Chem Rev 114(21):11060-11082 (Oct. 10, 2014).
Sutherland and Durand, Recent Results Cancer Res 95:24-49 (1984).
Tang et al., "Recent developments in deep eutectic solvents in chemical sciences" Monatsh Chem. 144:1427-1454 ( 2013).
Written Opinion for PCT/EP2017/052318.
Zhang et al., "Deep eutectic solvents: syntheses, properties and applications" Chem Soc Rev 41:7108-7146 (2012).
Zhao et al., "Choline-based deep eutectic solvents for enzymatic preparation of biodiesel from soybean oil" Journal of Molecular Catalysis B: Enzymatic 85-86:243-247 (2013).
Zhao et al., "Protease activation in glycerol-based deep eutectic solvents" J Mol Catal B Enzym. 72:163-167 ( 2011).
Bierne et al., "Inactivation of the srtA gene in Listeria monocytogenes inhibits anchoring of surface proteins and affects virulence" Molecular Microbiology 43(4):869-881 ( 2002).
Bolken et al., "Inactivation of the srtA gene in *streptococcus gordonii* inhibits cell wall anchoring of surface proteins and decreases in vitro and in vivo adhesion" Infection and Immunity 69(1):75-80 ( 2001).
Chan et al., "Covalent attachment of proteins to solid supports and surfaces via sortase-mediated ligation" PlosOne(11):e1164 ( 2007).
Dhar et al., "Anchor Structure of cell wall surface proteins in listeria monocytogenes" Biochemistry 39(13):3725-3733 ( 2000).
Fischetti et al., "Conservation of a hexapeptide sequence in the anchor region of surface proteins from Gram-positve cocci" Molecular Microbiology 4(9):1603-1605 ( 1990).
Glaser et al., "Comparative genomics of listeria species" Science 294:849-852 ( 2001).
Ilangovan et al., "Structure of sortase, the transpeptidase that anchors proteins to the cell wall of *Staphylococcus aureus*" Proceedings of the National Academy of Sciences 98(11):6056-6061 ( 2001).
Kruger et al., "Analysis of the substrate specificity of the *staphylococcus aureus* sortase transpeptidase SrtA" Biochemistry 43(6):1541-1551 ( 2004).
Mao et al., "Sortase-Mediated protein ligation: A new method for protein engineering" Journal of American Chemical Society 126:2670-2671 ( 2004).
Mazmanian et al., "Sortase-catalysed anchoring of surface proteins to the cell wall of *Staphylococcus aureus*" Molecular Microbiology 40(5):1049-1057 ( 2001).
Mazmanian et al., "*Staphylococcus aureus* Sortase, an enzyme that anchors surface proteins to the cell wall" Science 285:760-763 ( 1999).
Pallen et al., "An Embarrassment of sortases—a richness of substrates?" Trends in Microbiology 9(3):97-101 ( 2001).
Parthasarathy et al., Bioconjugate Chem 18:469-476 ( 2007).
Samantaray et al., "Peptide-sugar ligation catalyzed by transpeptidase sortase: A facile approach to neoglycoconjute synthesis" Journal Am. Chem. Soc. 130:2132-2133 ( 2008).
Dawson et al., "Synthesis of Native Proteins by Chemical Ligation" Annu. Rev. Biochem 69:923-60 ( 2000).
Jiang et al., "Research Progress on Sortase and its Application in Biotechnology" Current Biotechnology 1(3):184-188 ( 2011).
Yan et al., "Synthesis of Peptides and Proteins without Cysteine Residues by Native Chemical Ligation Combined with Desulfurization" Journal Am. Chem. Soc. 123:526-533 ( 2001).
Swee et al., "Sortase-meditated modification of αDEC205 affords optimization of antigen presentation and immunization against a set of viral epitopes" PNAS 110(4):1428-1433 ( 2013).
Tanaka et al., "Site-Specific Protein Modification on Living Cells Catalyzed by Sortase" ChemBioChem 9:802-807 ( 2008).
Witte et al., "Preparation of unnatural N-to-N and C-to-C protein fusions" PNAS 109(30):11993-11998 ( 2012).

\* cited by examiner

ACTIVITY ASSAY FOR BOND FORMING ENZYMES

CROSS REFERENCE TO RELATED APPLICATIONS

This application is a continuation of International Patent Application No. PCT/EP2015/079615 filed Dec. 14, 2015, which claims priority benefit to European Patent Application No. 14198535.8 filed Dec. 17, 2014, each of which are hereby incorporated by reference in their entireties.

SEQUENCE LISTING

The instant application contains a Sequence Listing submitted via EFS-Web and is hereby incorporated by reference in its entirety. Said ASCII copy, created Aug. 22, 2017, is named P32478_US_Substitute_Sequence_Listing.txt, and is 2,146 bytes in size.

FIELD OF THE INVENTION

The present invention generally relates to the detection of the presence and/or activity of a bond forming enzyme. The present invention in particular relates to the detection of the presence and/or activity of a sortase.

Background of the Invention

Bond forming enzymes, like sortases and transglutaminases, become more and more relevant in industrial and biotransformation processes. To use enzymes as a production tool, it is necessary to determine their properties.

Enzyme assays are methods to determine the activity of certain enzymes. This is necessary to study enzyme specificity or kinetics. Enzymes, that process chromogenic or fluorogenic substrates or cofactors like NAD are easy to monitor. These assays are known for quite a while and standard activity assays have been developed for multiple enzymes. Most of these assays are quick and easy to perform. However many enzymes do not use chromogenic or fluorogenic substrates or cofactors. This is true e.g. for the bond forming enzyme sortase, which is used herein as a representative for bond forming enzymes in general.

Various methods are published to monitor bond forming enzymatic reactions. Generally used are mass spectrometry or HPLC to determine weight or hydrophobicity changes between educts and products. However, these methods are complex, time consuming and difficult to perform in parallel. In addition, SDS-PAGE can be used to study differences in size of educts and products of bond forming enzymatic reactions.

In an early study of the sortase reaction (Ton-That et al., PNAS 96 (1999) 12424-12429) a combination of SDS-Gel and HPLC analysis is performed in a solely qualitative study without any kinetic data. In Ton-That et al. (J Biol Chem 275 (2000) 9876-9881) kinetic data of a sortase reaction is shown. Therein a combination of mass spectrometry, HPLC and absorbance measurements is used. However it is not possible to monitor the transpeptidation reaction because the signal solely comes from the cleavage of the LPETG substrate.

In Li et al. (Chinese Journal of Biotechnology 30(2) (2014) 284-293) a reporter system monitoring Sortase A catalyzed protein ligation efficiency via SDS-PAGE is reported.

Oteng-Pabi et al., (Analytical Biochemistry 441 (2013) 169-173) report continuous enzyme-coupled assay for microbial transglutaminase activity via released NH3.

In Matsumoto et al. (Journal of Biotechnology 152 (2011) 37-42) site-specific tetrameric streptavidin-protein conjugation using sortase A is reported.

Insight into the kinetic mechanism and evidence for a reverse protonation catalytic mechanism in Staphylococcus aureus Sortase Transpeptidase SrtA is described in Frankel et al. (Biochemistry 44 (2005) 11188-11200).

Thus, there is a need to provide a fast, reliable, efficient, sensitive, reproducible and easy to perform assay for the detection of bond forming enzymes.

SUMMARY OF THE INVENTION

Herein is reported a method and an assay for the detection of the presence and/or the activity of a bond forming enzyme, especially of a sortase.

In more detail it has been found that by the method of the current invention an assay to detect the activity of a bond forming enzyme can be established, which is faster, more sensitive, reproducible, reliable and/or suitable for a rapid screening compared to methods commonly used. In the method reported herein, among other things not only partial reactions can be measured like it is the case for some commercially available sortase assays where only the first cleavage reaction is detectable. Instead, in the current invention, the activity of a bond forming enzyme can only be detected if the full reaction has occurred. It has been found that for example by detecting the successful ligation reaction of a reporter enzyme to an entity which itself can be bound to a solid phase (e.g. a multiwell plate or a bead), the activity of a bond forming enzyme e.g. a sortase can be detected. The method as reported herein has improved properties with respect to currently known methods, such as high-performance liquid chromatography (HPLC)-based methods or that reported in Matsumoto et al. (Langmuir 28 (2012) 3553-3557) wherein at least one of speed, complexity, robustness, reproducibility, and sensitivity is improved.

One aspect as reported herein is a method for the detection of a bond forming enzyme in a sample, comprising the following steps:
  a) incubating the sample with a first substrate comprising an immobilization tag and a second substrate comprising a detectable label, whereby in the presence of a bond forming enzyme in the sample a conjugate comprising the immobilization tag and the detectable label is formed,
  b) immobilizing the conjugate (of step a)) via/using the immobilization tag to a solid phase,
  c) detecting the immobilized conjugate via/using the detectable label
and thereby detecting the bond forming enzyme (in the sample).

In one embodiment of all aspects as reported herein after the incubation (of step a)) additionally the sample is centrifuged.

One aspect as reported herein is a method for the detection of a bond forming enzyme in a sample, comprising the following steps:
  a) incubating the sample with a first substrate comprising an immobilization tag and a second substrate comprising a detectable label, whereby in the presence of a bond forming enzyme in the sample a conjugate comprising the immobilization tag and the detectable label is formed, i.e. the first substrate is conjugated to the second substrate,
b) centrifuging the sample,
c) immobilizing the conjugate (of step a)) via/using the immobilization tag to a solid phase,
d) detecting the immobilized conjugate via/using the detectable label and thereby detecting the bond forming enzyme in the sample.

In one embodiment of all aspects as reported herein after the incubation (of step a)) additionally the sample is centrifuged between 5 min and 15 min and at between 2500×g to 7500×g.

In one embodiment of all aspects as reported herein the presence of a (functional) bond forming enzyme is detected (qualitative detection).

In one embodiment of all aspects as reported herein the degree of activity of a bond forming enzyme is determined (quantitative detection).

In one embodiment of all aspects as reported herein the first substrate comprising an immobilization tag comprises a first bond forming enzyme recognition motif and the second substrate comprising a detectable label comprises a second bond forming enzyme recognition motif.

In one embodiment of all aspects as reported herein the first bond forming enzyme recognition motif is a first sortase recognition motif and the second bond forming enzyme recognition motif is a second sortase recognition motif.

In one embodiment of all aspects as reported herein
1) the first sortase recognition motif comprises an LPXTG motif (SEQ ID NO: 01), wherein X represents any amino acid and the second sortase recognition motif comprises an oligoglycine (e.g. SEQ ID NO: 03; GGG) or oligoalanine motif (e.g. SEQ ID NO: 04; AAA), or
2) the second sortase recognition motif comprises an LPXTG motif (SEQ ID NO: 01), wherein X represents any amino acid and the first sortase recognition motif comprises an oligoglycine (e.g. SEQ ID NO: 03; GGG) or oligoalanine motif (e.g. SEQ ID NO: 04; AAA).

In one embodiment of all aspects as reported herein the detectable label is a protein, a fluorophore, a radioactive element, a nanoparticle or a colorimetric dye.

In one embodiment of all aspects as reported herein the detectable label is an enzyme.

In one embodiment of all aspects as reported herein the detectable label is a enzyme catalyzing a colorimetric reaction.

In one embodiment of all aspects as reported herein the detectable label is a glucose dehydrogenase.

In one embodiment of all aspects as reported herein the immobilization tag is a first member of a specific binding pair and the solid phase is conjugated to the second member of the specific binding pair.

In one embodiment of all aspects as reported herein the immobilization tag is biotin and the solid phase is conjugated to streptavidin or avidin.

In one embodiment of all aspects as reported herein the solid phase is a multiwell plate.

In one embodiment of all aspects as reported herein the solid phase is a bead.

In one embodiment of all aspects as reported herein after the incubation (of step a)) additionally the sample is diluted between 10 times and 30 times.

In one embodiment of all aspects as reported herein after the incubation (of step a)) additionally the sample is diluted between 15 times and 25 times.

In one embodiment of all aspects as reported herein after the incubation (of step a)) additionally the sample is diluted about 1:20 (20 times).

In one embodiment of all aspects as reported herein after the incubation (of step a)) additionally the sample is diluted with a solution comprising iodacetamide (IAA).

In one embodiment of all aspects as reported herein after the incubation (of step a)) iodacetamide (IAA) is added.

In one embodiment of all aspects as reported herein after the immobilization (of step b) or c), respectively) additionally the sample is washed at least 3 times.

In one embodiment of all aspects as reported herein after the immobilization (of step b) or c), respectively) additionally the sample is washed 4 to 12 times.

In one embodiment of all aspects as reported herein after the immobilization (of step b) or c), respectively) additionally the sample is washed 6 to 10 times.

In one embodiment of all aspects as reported herein the bond forming enzyme is a sortase.

One aspect as reported herein is a method for the detection of a sortase in a sample, comprising the following steps:
a) incubating the sample with a first substrate comprising an immobilization tag and a second substrate comprising a detectable label, whereby in the presence of a sortase in the sample a conjugate comprising the immobilization tag and the detectable label is formed,
b) immobilizing the conjugate (of step a)) via/using the immobilization tag to a solid phase,
c) detecting the immobilized conjugate via/using the detectable label and thereby detecting the sortase in the sample.

In one embodiment of all aspects as reported herein after the incubation (of step a)) additionally the sample is centrifuged.

One aspect as reported herein is a method for the detection of a sortase in a sample, comprising the following steps:
a) incubating the sample with a first substrate comprising an immobilization tag and a second substrate comprising a detectable label, whereby in the presence of a sortase in the sample a conjugate comprising the immobilization tag and the detectable label is formed, i.e. the first substrate is conjugated to the second substrate,
b) centrifuging the sample,
c) immobilizing the conjugate (of step a)) via/using the immobilization tag to a solid phase,
d) detecting the immobilized conjugate via/using the detectable label and thereby detecting the sortase in the sample.

In one embodiment of all aspects as reported herein after the incubation (of step a)) additionally the sample is centrifuged between 5 min and 15 min and at between 2500×g to 7500×g.

In one embodiment of this aspect the presence of a (functional) sortase is detected (qualitative detection).

In one embodiment of this aspect the degree of activity of a sortase is determined (quantitative detection).

In one embodiment of this aspect the first substrate comprising an immobilization tag comprises a first sortase recognition motif and the second substrate comprising a detectable label comprises a second sortase recognition motif.

In one embodiment of this aspect
1) the first sortase recognition motif comprises an LPXTG motif (SEQ ID NO: 01), wherein X represents any amino acid and the second sortase recognition motif comprises an oligoglycine (e.g. SEQ ID NO: 03; GGG) or oligoalanine motif (e.g. SEQ ID NO: 04; AAA) or 2) the second sortase recognition motif comprises an LPXTG motif (SEQ ID NO: 01), wherein X represents any amino acid and the first sortase recognition motif comprises an oligoglycine (e.g. SEQ ID NO: 03; GGG) or oligoalanine motif (e.g. SEQ ID NO: 04; AAA).

In one embodiment of all aspects as reported herein after the incubation (of step a)) additionally the sample is diluted between 10 times and 30 times.

In one embodiment of all aspects as reported herein after the incubation (of step a)) additionally the sample is diluted between 15 times and 25 times.

In one embodiment of all aspects as reported herein after the incubation (of step a)) additionally the sample is diluted about 1:20 (20 times).

In one embodiment of all aspects as reported herein after the incubation (of step a)) additionally the sample is diluted with a solution comprising iodacetamide (IAA).

In one embodiment of all aspects as reported herein after the incubation (of step a)) iodacetamide (IAA) is added.

One aspect as reported herein is a method for selecting a bond forming enzyme from a multitude of bond forming enzymes by
 a) providing at least two bond forming enzymes
 b) performing the method as reported herein with the at least two of bond forming enzymes,
 c) selecting a bond forming enzyme detected in step b).

In one embodiment of this aspect the bond forming enzyme with the highest activity is selected.

One aspect as reported herein is a method for selecting a sortase from a multitude of sortases by
 a) providing at least two sortases
 b) performing the method as reported herein with the at least two sortases,
 c) selecting a sortase detected in step b).

In one embodiment of this aspect the sortase with the highest activity is selected.

One aspect as reported herein is a bond forming assay for detecting a bond forming enzyme in a sample, comprising the following steps:
 a) incubating the sample with a first substrate comprising an immobilization tag and a second substrate comprising a detectable label, whereby in the presence of a bond forming enzyme in the sample a conjugate comprising the immobilization tag and the detectable label is formed,
 b) immobilizing the conjugate (of step a)) via/using the immobilization tag to a solid phase,
 c) detecting the immobilized conjugate via/using the detectable label and thereby detecting the bond forming enzyme (in the sample).

DETAILED DESCRIPTION OF THE INVENTION

It has been found that an improved assay for the detection of the activity of an bond forming enzyme can be established by the method of this invention.

By using a system, which detects the full/complete reaction of a bond forming enzyme and making use of first substrate comprising an immobilization tag (e.g. biotin, streptavidin), which comprises a first bond forming enzyme recognition motif and a second substrate comprising a detectable label, (e.g. a reporter enzyme), which comprises a second bond forming enzyme recognition motif, an improved activity assay can be provided.

The improvements being without limitation in speed, availability for rapid screening, sensitivity and costs for material and equipment.

With the method as reported herein, e.g. the kinetics of a sortase can be measured directly (e.g. photometrically) by fusing a reporter enzyme to different recognition motives of a sortase and using this as a first substrate. As a second substrate, e.g. biotinylated glycin or alanine is used as a nucleophile. If the sortase is added to first and the second substrate, the product is a biotinylated reporter enzyme. This product can be attached to a solid phase e.g a streptavidin-coated multiwell plate (SA-MTP) via the biotin. When a substrate for the reporter enzyme is added, the product can be detected.

Referring to the quantity of the activity of the reporter enzyme, one can draw conclusions about the activity of the bond forming enzyme, since only biotinylated reporter enzyme is bound to the SA-MTP after washing. I can be concluded, that the better the bond forming enzyme labels the reporter enzyme with biotin, the more reporter enzyme-biotin can be immobilized on the SA-MTP and a higher turnover of the substrate can be detected.

Herein is reported a method for the detection of a bond forming enzyme in a sample, comprising the following steps:
 a) incubating the sample with a first substrate comprising an immobilization tag and a second substrate comprising a detectable label, whereby in the presence of a bond forming enzyme in the sample a conjugate comprising the immobilization tag and the detectable label is formed,
 b) immobilizing the conjugate of step a) via/using the immobilization tag to a solid phase,
 c) detecting the immobilized conjugate via/using the detectable label
and thereby detecting the bond forming enzyme (in the sample).

The term "bond-forming enzyme," as used herein, refers to any enzyme that catalyzes a reaction resulting in the formation of a covalent bond. In one embodiment the bond forming enzyme is a amide bond forming enzyme. In one preferred embodiment the bond forming enzyme is a peptide bond forming enzyme. In one preferred embodiment, the bond forming enzyme is a sortase. In some embodiments, the bond-forming enzyme is a ligase, a polymerase, a kinase, an aldolase, a diels alderase, or a transferase (e.g. transglutaminase, glycosyltransferase, ADP-Ribosyltransferase, hydrolases in water free solvents).

The term "conjugated" or "conjugation" refers to an association of two entities, for example, of two molecules such as two proteins, or a protein and a reactive handle, or a protein and an agent, e.g., a detectable label. The association can be, for example, via a direct or indirect (e.g., via a linker) covalent linkage or via non-covalent interactions. In some embodiments, the association is covalent. In some embodiments, two molecules are conjugated via a linker connecting both molecules. For example, in some embodiments where two proteins are conjugated to each other to form a protein fusion, the two proteins may be conjugated via a polypeptide linker, e.g., an amino acid sequence connecting the C-terminus of one protein to the N-terminus of the other protein. In some embodiments, conjugation of a protein to a protein or peptide is achieved by transpeptidation using a sortase. See, e.g., WO2010/087994 and WO/2011/133704, the entire contents of each of which are incorporated herein by reference, for exemplary sortases, proteins, recognition motifs, reagents, and methods for sortase-mediated transpeptidation.

The term "agent," as used herein, refers to any molecule, entity, or moiety. For example, an agent may be a protein, an amino acid, a peptide, a polynucleotide, a carbohydrate, a lipid, a detectable label, a binding agent, a tag, a metal atom, a contrast agent, a catalyst, a non-polypeptide polymer, a synthetic polymer, a recognition element, an immobilization tag, a linker, or chemical compound, such as a small molecule.

The term "detectable label" refers to a moiety that has at least one element, isotope, or functional group incorporated into the moiety which enables detection of the molecule, e.g., a protein or peptide, or other entity, to which the label is attached. Labels can be directly attached or can be attached via a linker. It will be appreciated that the label may be attached to or incorporated into a molecule, for example, a protein, polypeptide, or other entity, at any position. In one embodiment of all aspects as reported herein the detectable label is a protein, a fluorophore, a radioactive element, a nanoparticle or a colorimetric dye. In one embodiment of all aspects as reported herein the detectable label is an enzyme. In one embodiment of all aspects as reported herein the detectable label is an enzyme catalyzing a colorimetric reaction. In one embodiment of all aspects as reported herein the detectable label is a glucose dehydrogenase.

Chromogens (fluorescent or luminescent groups and dyes), enzymes, e.g. glucose dehydrogenase, NMR-active groups or metal particles, haptens, e.g. digoxigenin, or binding agents, e.g. antibodies are examples of detectable labels. The detectable label can also be a photoactivatable crosslinking group, e.g. an azido or an azirine group. Metal chelates which can be detected by electrochemoluminescence (ECL) are also preferred signal-emitting groups, with particular preference being given to ruthenium chelates, e.g. a ruthenium (bispyridyl)32+ chelate. Suitable ruthenium labeling groups are described, for example, in EP 0 580 979, WO 90/05301, WO 90/11511, and WO 92/14138.

The term "immobilization tag" as used herein, refers to a moiety suitable to be immobilized on a solid phase. In one embodiment the immobilization tag is selected from the group comprising Streptavidin-Tag (Strep-Tag), Biotin-Tag, Histidin-Tag (His-Tag), Avidin-Tag (Avi-Tag) HaloTag, ProteinA, FLAG-Tag, Cellulose binding module, Maltose-binding protein, Tamavidin, antigene which can be bound by an antibody.

The term "sample" includes, but is not limited to, any quantity of a substance from a living thing or formerly living thing. Such living things include, but are not limited to, humans, mice, monkeys, rats, rabbits, and other animals. Such substances include, but are not limited to, whole blood, serum, or plasma from an individual, which are the most widely used sources of sample in clinical routine. In one embodiment the sample is a lysate from a population of bacterial cells, e.g. from Staphylococcus aureus (S. aureus) cells.

The term "small molecule" is used herein to refer to molecules, whether naturally-occurring or artificially created (e.g., via chemical synthesis) that have a relatively low molecular weight. Typically, a small molecule is an organic compound (i.e., it contains carbon). A small molecule may contain multiple carbon-carbon bonds, stereocenters, and other functional groups (e.g., amines, hydroxyl, carbonyls, or heterocyclic rings).

The term "solid phase" means a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; multiwell plates; solid strips; and cuvettes, tubes or other spectrometer sample containers. A solid phase component of an assay is distinguished from inert solid surfaces with which the assay may be in contact in that a "solid phase" contains at least one moiety on its surface, which is intended to interact with the capture drug antibody. A solid phase may be a stationary component, such as a tube, strip, cuvette or multiwell plate, or may be non-stationary components, such as beads and microparticles. Microparticles can also be used as a solid phase for homogeneous assay formats. A variety of microparticles that allow either non-covalent or covalent attachment of proteins and other substances may be used. Such particles include polymer particles such as polystyrene and poly(methylmethacrylate); gold particles such as gold nanoparticles and gold colloids; and ceramic particles such as silica, glass, and metal oxide particles. See for example Martin, C. R., et al., Analytical Chemistry-News & Features, May 1, 1998, 322A-327A, which is incorporated herein by reference. In one embodiment of all aspects as reported herein the solid phase is a multiwell plate. In one embodiment of all aspects as reported herein the solid phase is a bead.

The term "substrate," as used herein refers to a molecule or entity that can be utilized in a bond forming enzyme-mediated conjugation reaction. Typically, a bond forming enzyme utilizes two substrates. For example, the first substrate comprises a (in one preferred embodiment C-terminal) bond forming enzyme recognition motif, and the second substrate comprises an (in one preferred embodiment N-terminal) bond forming enzyme recognition motif and the reaction results in a conjugation of both substrates via a covalent bond.

A substrate may comprise additional moieties or entities apart from the recognition motif. For example, a substrate may comprise a first bond forming enzyme recognition motif, the e.g. N-terminus of which is conjugated to any agent, e.g., a peptide or protein, a small molecule, a binding agent, a lipid, a carbohydrate, a detectable label or an immobilization tag. Likewise, a substrate may comprise a second bond forming enzyme recognition motif, the e.g. C-terminus of which is conjugated to any agent, e.g., a peptide or protein, a small molecule, a binding agent, a lipid, a carbohydrate, a detectable label or an immobilization tag. Accordingly, substrates are not limited to proteins or peptides but include any moiety or entity conjugated to a sortase recognition motif One exemplary recognition motif is a sortase recognition motif. Some sortase recognition motifs are described herein and additional suitable sortase recognition motifs are well known to those of skill in the art. For example, sortase A of S. aureus recognizes and utilizes a C-terminal LPXTG motif (SEQ ID NO: 01) and an N-terminal GG(G) motif in transpeptidation reactions. Additional sortase recognition motifs will be apparent to those of skill in the art, and the invention is not limited in this respect.

Other methods like mass spectrometry (MS), high-performance liquid chromatography (HPLC) or SDS page are being reported that might be able to detect the full reaction of a bond forming enzyme (mainly by detecting differences in size), but these are complex and slow. The following table provides a comparison of different method with the method of the current invention and shows the superiority in speed for the method of the invention.

| Methods | Parallel measurements | Estimated amount of measurements per 5 h |
|---|---|---|
| HPLC | 1 | ~10 |
| MS | 1 | ~15 |
| SDS-PAGE | 15 | ~180 |
| Method of the invention (beads) | 96 | ~1536 |
| Method of the invention (multiwell plate) | 96 | ~3072 |

It also has been found that the method of the current invention is more sensitive than other methods commonly used. For example it is know by a person skilled in the art, that by HPLC, MS or SDS-PAGE a sensitivity of less than 1% of yield/turnover/ligated product cannot be achieved. However this is possible with the method of the invention (see FIG. 1). Also when compared to other methods e.g. as described by Matsumoto et al. (2012), an improvement in sensitivity can be achieved by the method as reported herein (see FIGS. 3 and 4).

In one embodiment of all aspects as reported herein the presence of a (functional) bond forming enzyme is detected (qualitative detection).

In one embodiment of all aspects as reported herein the degree of activity of a bond forming enzyme is determined (quantitative detection).

In one embodiment of all aspects as reported herein the first substrate comprising an immobilization tag comprises a first bond forming enzyme recognition motif and the second substrate comprising a detectable label comprises a second bond forming enzyme recognition motif. In one embodiment of all aspects as reported herein the first bond forming enzyme recognition motif is a first sortase recognition motif and the second bond forming enzyme recognition motif is a second sortase recognition motif.

In one embodiment of all aspects as reported herein
1) the first sortase recognition motif comprises an LPXTG motif (SEQ ID NO: 01), wherein X represents any amino acid and the second sortase recognition motif comprises an oligoglycine (e.g. SEQ ID NO: 03; GGG) or oligoalanine motif (e.g. SEQ ID NO: 04; AAA), or
2) the second sortase recognition motif comprises an LPXTG motif (SEQ ID NO: 01), wherein X represents any amino acid and the first sortase recognition motif comprises an oligoglycine (e.g. SEQ ID NO: 03; GGG) or oligoalanine motif (e.g. SEQ ID NO: 04; AAA).

In one embodiment of the invention the immobilization tag is a first member of a specific binding pair and the solid phase is conjugated to the second member of the specific binding pair. Such a specific binding pair (first member/ second member) is, for example, streptavidin or avidin/ biotin, antibody/antigen (see, for example, Hermanson, G. T., et al., Bioconjugate Techniques, Academic Press, 1996), lectin/polysaccharide, steroid/steroid binding protein, hormone/hormone receptor, enzyme/substrate, IgG/Protein A and/or G and/or L, etc. In one preferred embodiment of all aspects as reported herein the immobilization tag is biotin and the solid phase is conjugated to streptavidin or avidin.

It has been found that the reliability, reproducibility and robustness of the method can be improved inter alia by diluting the sample prior to immobilizing on a solid phase and by centrifuging the sample. Further, reliability, reproducibility and robustness can be improved by stopping the bond forming enzyme-mediated reaction with a suitable agent.

In one embodiment of all aspects as reported herein after the incubation of step a) additionally the sample is diluted with a solution comprising iodacetamide (IAA). In one embodiment of all aspects as reported herein after the incubation of step a) additionally the sample is diluted between 10 times and 30 times. In one embodiment of all aspects as reported herein after the incubation of step a) additionally the sample is diluted between 15 times and 25 times. In one embodiment of all aspects as reported herein after the incubation of step a) additionally the sample is diluted about 1:20 (20 times).

In one embodiment of all aspects as reported herein after the incubation of step a) additionally the sample is centrifuged. In one embodiment of all aspects as reported herein after the incubation of step a) additionally the sample is centrifuged between 5 min and 15 min and at between 2500×g to 7500×g.

It has been found that the reliability and robustness of the method can further be improved by washing the sample prior to detecting the immobilized conjugate.

In one embodiment of all aspects as reported herein after the immobilization of step b) additionally the sample is washed at least 3 times. In one embodiment of all aspects as reported herein after the immobilization of step b) additionally the sample is washed 4 to 12 times. In one embodiment of all aspects as reported herein after the immobilization of step b) additionally the sample is washed 6 to 10 times.

The term "sortase," as used herein, refers to a protein having sortase activity, i.e., an enzyme able to carry out a transpeptidation reaction conjugating the C-terminus of a protein to the N-terminus of a protein or an 6-amino-group of lysine via transamidation. The term includes full-length sortase proteins, e.g., full-length naturally occurring sortase proteins, fragments of such sortase proteins that have sortase activity, modified (e.g., mutated) variants or derivatives of such sortase proteins or fragments thereof, as well as proteins that are not derived from a naturally occurring sortase protein, but exhibit sortase activity. Those of skill in the art will readily be able to determine whether or not a given protein or protein fragment exhibits sortase activity, e.g., by contacting the protein or protein fragment in question with a suitable sortase substrate under conditions allowing transpeptidation and determining whether the respective transpeptidation reaction product is formed.

Suitable sortases will be apparent to those of skill in the art and include, but are not limited to sortase A, sortase B, sortase C, and sortase D type sortases. For example, the present invention encompasses embodiments relating to a sortase A from any bacterial species or strain. The invention encompasses embodiments relating to a sortase B from any bacterial species or strain. The invention encompasses embodiments relating to a class C sortase from any bacterial species or strain. The invention also encompasses embodiments relating to a class D sortase from any bacterial species or strain. Amino acid sequences of sortases and the nucleotide sequences that encode them are known to those of skill in the art. Those of skill in the art will appreciate that any sortase and any sortase recognition motif can be used in some embodiments of this invention. In some embodiments, the sortase is a sortase A of *S. aureus*. In some embodiments, the sortase is a sortase A of another organism, for example, from another bacterial strain, such as *S. pyogenes, L. monozytogenes* or *G. haemolysans*. In some embodiments, the sortase is a sortase B, a sortase C, or a sortase D. Suitable sortases from other bacterial strains will be apparent to those of skill in the art.

Herein is reported a method for the detection of a sortase in a sample, comprising the following steps:

a) incubating the sample with a first substrate comprising an immobilization tag and a second substrate comprising a detectable label, whereby in the presence of a sortase in the sample a conjugate comprising the immobilization tag and the detectable label is formed,
b) immobilizing the conjugate of step a) via/using the immobilization tag to a solid phase,
c) detecting the immobilized conjugate via/using the detectable label and thereby detecting the sortase in the sample.

In one embodiment of this aspect the presence of a (functional) sortase is detected (qualitative detection).

In one embodiment of this aspect the degree of activity of a sortase is determined (quantitative detection).

In one embodiment of this aspect the first substrate comprising an immobilization tag comprises a first sortase recognition motif and the second substrate comprising a detectable label comprises a second sortase recognition motif.

In one embodiment of this aspect
1) the first sortase recognition motif comprises an LPXTG motif (SEQ ID NO: 01), wherein X represents any amino acid and the second sortase recognition motif comprises an oligoglycine (e.g. SEQ ID NO: 03; GGG) or oligoalanine motif (e.g. SEQ ID NO: 04; AAA) or
2) the second sortase recognition motif comprises an LPXTG motif (SEQ ID NO: 01), wherein X represents any amino acid and the first sortase recognition motif comprises an oligoglycine (e.g. SEQ ID NO: 03; GGG) or oligoalanine motif (e.g. SEQ ID NO: 04; AAA).

In one embodiment of all aspects as reported herein the detectable label is a protein, a fluorophore, a radioactive element, a nanoparticle or a colorimetric dye. In one embodiment of this aspect the detectable label is an enzyme. In one embodiment of this aspect the detectable label is an enzyme catalyzing a colorimetric reaction. In one embodiment of this aspect the detectable label is a glucose dehydrogenase.

In one embodiment of this aspect the immobilization tag is a first member of a specific binding pair and the solid phase is conjugated to the second member of the specific binding pair. In one embodiment of this aspect the immobilization tag is biotin and the solid phase is conjugated to streptavidin or avidin.

In one embodiment of this aspect the solid phase is a multiwell plate. In one embodiment of this aspect the solid phase is a bead.

In one embodiment of this aspect after the incubation of step a) additionally the sample is diluted with a solution comprising iodacetamide (IAA). In one embodiment of all aspects as reported herein after the incubation of step a) additionally the sample is diluted between 10 times and 30 times. In one embodiment of all aspects as reported herein after the incubation of step a) additionally the sample is diluted between 15 times and 25 times. In one embodiment of all aspects as reported herein after the incubation of step a) additionally the sample is diluted about 1:20 (20 times).

In one embodiment of this aspect after the incubation of step a) additionally the sample is centrifuged. In one embodiment of this aspect after the incubation of step a) additionally the sample is centrifuged between 5 min and 15 min and at between 2500×g to 7500×g.

In one embodiment of this aspect after the immobilization of step b) additionally the sample is washed at least 3 times. In one embodiment of this aspect after the immobilization of step b) additionally the sample is washed 4 to 12 times. In one embodiment of this aspect after the immobilization of step b) additionally the sample is washed 6 to 10 times.

Herein is reported a method for the detection of a bond forming enzyme in a sample, comprising the following steps:
a) incubating the sample with a first substrate comprising an immobilization tag and a second substrate comprising a detectable label, whereby in the presence of a bond forming enzyme in the sample a conjugate comprising the immobilization tag and the detectable label is formed,
b) immobilizing the conjugate of step a) via/using the immobilization tag to a solid phase,
c) detecting the immobilized conjugate via/using the detectable label and thereby detecting the bond forming enzyme (in the sample),
wherein the bond forming enzyme is a sortase, and wherein
1) the first sortase recognition motif comprises an LPXTG motif (SEQ ID NO: 01), wherein X represents any amino acid and the second sortase recognition motif comprises an oligoglycine (e.g. SEQ ID NO: 03; GGG) or oligoalanine motif (e.g. SEQ ID NO: 04; AAA) or
2) the second sortase recognition motif comprises an LPXTG motif (SEQ ID NO: 01), wherein X represents any amino acid and the first sortase recognition motif comprises an oligoglycine (e.g. SEQ ID NO: 03; GGG) or oligoalanine motif (e.g. SEQ ID NO: 04; AAA), and wherein the detectable label is a glucose dehydrogenase, and wherein the immobilization tag is biotin and the solid phase is conjugated to streptavidin or avidin, and wherein the solid phase is a multiwell plate or a bead, and wherein
after the incubation of step a) additionally the sample is diluted between 15 times and 25 times with a solution comprising iodacetamide (IAA), and wherein
after the incubation of step a) and the dilution additionally the sample is centrifuged between 5 min and 15 min and at between 2500×g to 7500×g, and wherein
after the immobilization of step b) additionally the sample is washed 6 to 10 times.

Herein reported is a method for selecting a bond forming enzyme from a multitude of bond forming enzymes by
a) providing at least two bond forming enzymes
b) performing the method as reported herein with the at least two of bond forming enzymes,
c) selecting a bond forming enzyme detected in step b).

In one embodiment of this aspect the bond forming enzyme with the highest activity, a defined specificitiy, a defined pH optimum, a defined temperature optimum or the highest activety after stress (e.g. induced by heat or pH) is selected. In one embodiment of this aspect the bond forming enzyme with the highest activity is selected.

Herein is reported a method for selecting a sortase from a multitude of sortases by
a) providing at least two sortases
b) performing the method as reported herein with the at least two sortases,
c) selecting a sortase detected in step b).

In one embodiment of this aspect the bond forming enzyme with the highest activity, a defined specificitiy, a defined pH optimum, a defined temperature optimum or the highest activety after stress (e.g. induced by heat or pH) is selected. In one embodiment of this aspect the sortase with the highest activity is selected.

Herein reported is a bond forming assay for detecting a bond forming enzyme in a sample, comprising the following steps:
a) incubating the sample with a first substrate comprising an immobilization tag and a second substrate comprising a detectable label, whereby in the presence of a bond forming enzyme in the sample a conjugate comprising the immobilization tag and the detectable label is formed,
b) immobilizing the conjugate of step a) via/using the immobilization tag to a solid phase,
c) detecting the immobilized conjugate via/using the detectable label and thereby detecting the bond forming enzyme (in the sample).

The following examples, figures and sequences are provided to aid the understanding of the present invention, the true scope of which is set forth in the appended claims. It is understood that modifications can be made in the procedures set forth without departing from the spirit of the invention.

DESCRIPTION OF THE SEQUENCE LISTING

SEQ ID NO: 01 Sortase motif LPXTG
SEQ ID NO: 02 Sortase motif LPXTA
SEQ ID NO: 03 Oligo-glycine GGG
SEQ ID NO: 04 Oligo-alanine AAA
SEQ ID NO: 05 Oligo-glycine attached to biotin (GG-biotin)
SEQ ID NO: 06 Oligo-glycine attached to streptavidin (GG-streptavidin)
SEQ ID NO: 07 Oligo-alanine attached to biotin (AA-biotin)
SEQ ID NO: 08 Oligo-alanine attached to streptavidin (AA-streptavidin)

EXAMPLE 1

Figure 1:
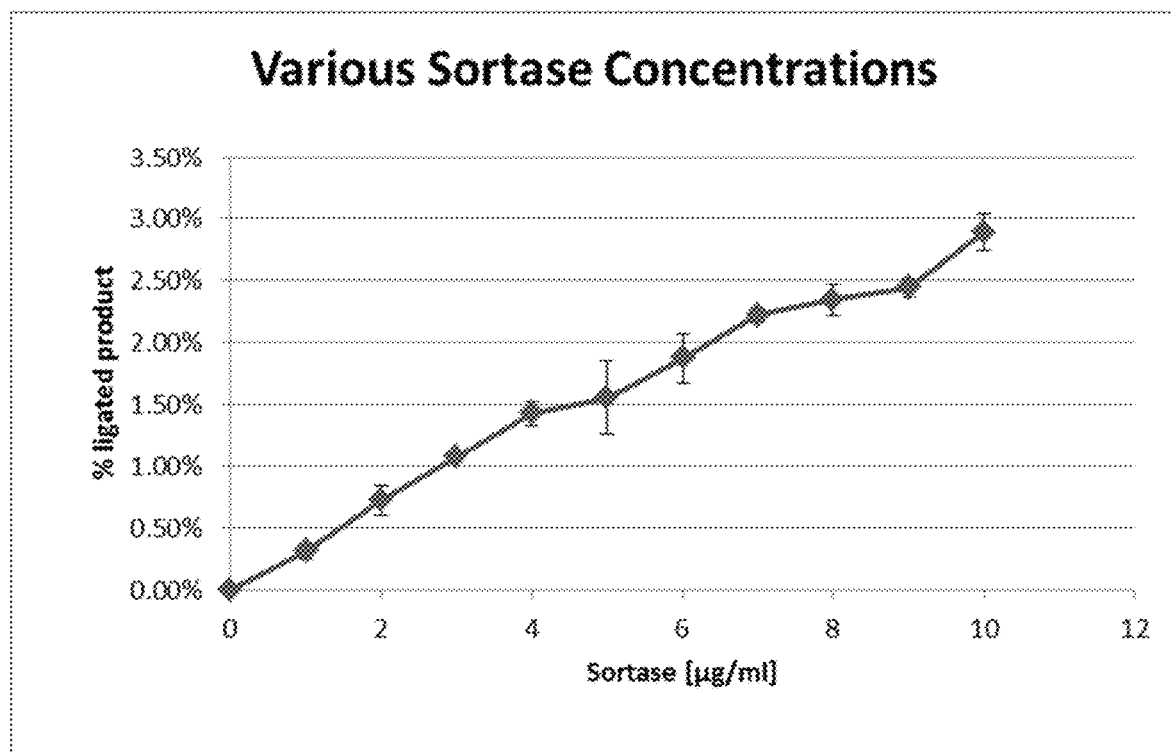
FIG. 1 Effect of Sortase concentration on ligation yield. Yield was determined based on protocol for measuring sortase activity (see example 2)
Figure 2:
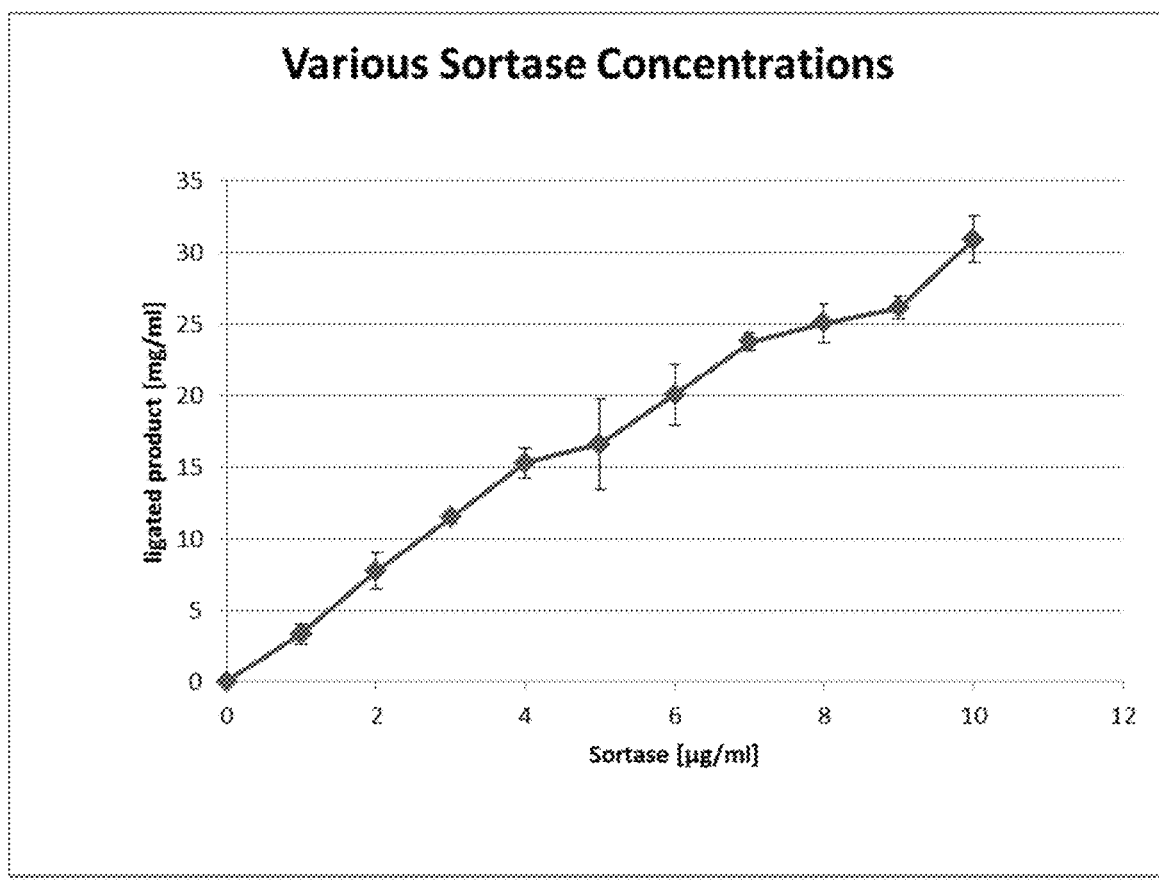
FIG. 2 Effect of Sortase concentration on product formation. Yield was determined based on protocol for measuring sortase activity (see example 2)

High Throughput Screening of Sortase Activity from Crude Lysate

Cells (*E. coli* BL21) expressing sortase are cultured in 96 well plates with 200 μL LB-media.

Each cell suspension is lysed with lysis buffer (50 mM Tris pH 7.5, 0.1% TritonX-100, 200 mM NaCl and 5% B-PER) mixing it 1:10 and incubated at 50° C. for 30 min.

50 μL of the lysate are mixed with 150 μL substrate solution (50 mM Tris pH 7.5, 200 mM NaCl, 20 μM of a glucose dehydrogenase (containing one of the substrates of the sortase reaction (LPXTG; here: X=K)) and 20 μM biotin (containing the other substrate of the sortase reaction (here: GGG))) and incubated for 2h at 37° C.

The reaction is stopped by addition of a 10- to 20-fold excess of inhibition buffer (50 μM Tris, pH 7.5, 200 μM NaCl, 10 mM $CaCl_2$, 5 mM iodoacetamide). The stopped reaction mixture is centrifuged for 10 min at 5000×g.

The supernatant (50 μL) is transferred to a streptavidin coated multiwell plate and 100 μL of 50 mM Tris buffer (pH 7.5) comprising 200 mM NaCl, 10 mM $CaCl_2$ is added and the mixture is incubated for 30 min at 30° C. at 200 rpm.

Thereafter the multiwell plate is washed eight times with 300 μL washing buffer each (50 mM Tris, pH 7.5, 200 mM NaCl, 10 mM $CaCl_2$, 5 mg/mL BSA, 0.1% Triton X-100).

After washing the multiwell plate 150 μL test buffer (0.2 M sodium citrate, pH 5.8, 0.3 g/L 4-nitrosoanilin, 1 mM CaCl2, 30 mM glucose) is added.

The kinetic of the reporter enzyme (glucose dehydrogenase) is measured over a time period of 5 min at 620 nm The activity of the reporter enzyme is proportional to the amount of immobilized enzyme which is proportional to the amount of biotinylated enzyme and this is proportional to the activity of the sortase.

EXAMPLE 2

Measuring Sortase Activity

Purified sortase is mixed with its two substrates, the reporter enzyme, i.e. a glucose dehydrogenase containing the LPXTG (here: X=K) motif (60 μm) and a biotin derivative containing N-terminal glycines or alanines (60 μm) (1:1:1) in 50 mM Tris buffer pH 7.5 containing 200 mM NaCl.

This reaction mixture is incubated at 37° C. for 2h.

The reaction was stopped by addition of a 10- to 20-fold excess of inhibition buffer (50 mM Tris, pH 7.5, 200 mM NaCl, 10 mM $CaCl_2$, 5 mM iodoacetamide).

The stopped reaction mixture is centrifuged for 10 min 5000×g.

The supernatant (50 μL) is added to 100 μL of 50 mM Tris buffer (pH 7.5) comprising 200 mM NaCl, 10 mM $CaCl_2$ and streptavidin coted magnetic beads are added and incubated for 30 min at 30° C. at 200 rpm.

Thereafter the magnetic beads are washed five times with 300 μL washing buffer each (50 mM Tris, pH 7.5, 200 mM NaCl, 10 mM $CaCl_2$, 5 mg/mL, BSA, 0.1% Triton X-100) in V-bottom multi-well plates using a magnet and a vacuum pump.

Afterwards the beads are resuspended in 100 μL citrate test buffer and 10-80 μL thereof are transferred to a new well. Thereto 150 μL test buffer (0.2 M sodium citrate, pH 5.8, 0.3 g/L 4-nitrosoanilin, 1 mM $CaCl_2$, 30 mM glucose) is added.

The kinetic of the reporter enzyme is measured over a time period of 5 min at 620 nm.

The activity of the reporter enzyme is proportional to the amount of immobilized enzyme, which is proportional to the amount of biotinylated enzyme and this is proportional to the activity of the sortase.

EXAMPLE 3

Measuring Sortase Activity with Different Method Setups

The experiments were basically performed as described above with some alterations:

Setup 1: method as described above (example 2)
Setup 2: like setup 1 but lacking the centrifugation step
Setup 3: like setup 2 but additionally also lacking the step of stopping the reaction by addition of IAA (iodoacetamid).
Setup 4: like setup 3 but additionally lacking the step of dilution step.

The substrate concentrations were chosen analog the publication of Matsumoto et al. (2011 and 2012) (5 µM Sort-tag LPKTG, 20 µM Nucleophile GGG-Biotin). The temperature, time of incubation and the enzyme concentration were chosen analog Matsumoto et al. (2012) (2.1 µM SrtA, 25 C° and 30 min).

Figure 3:
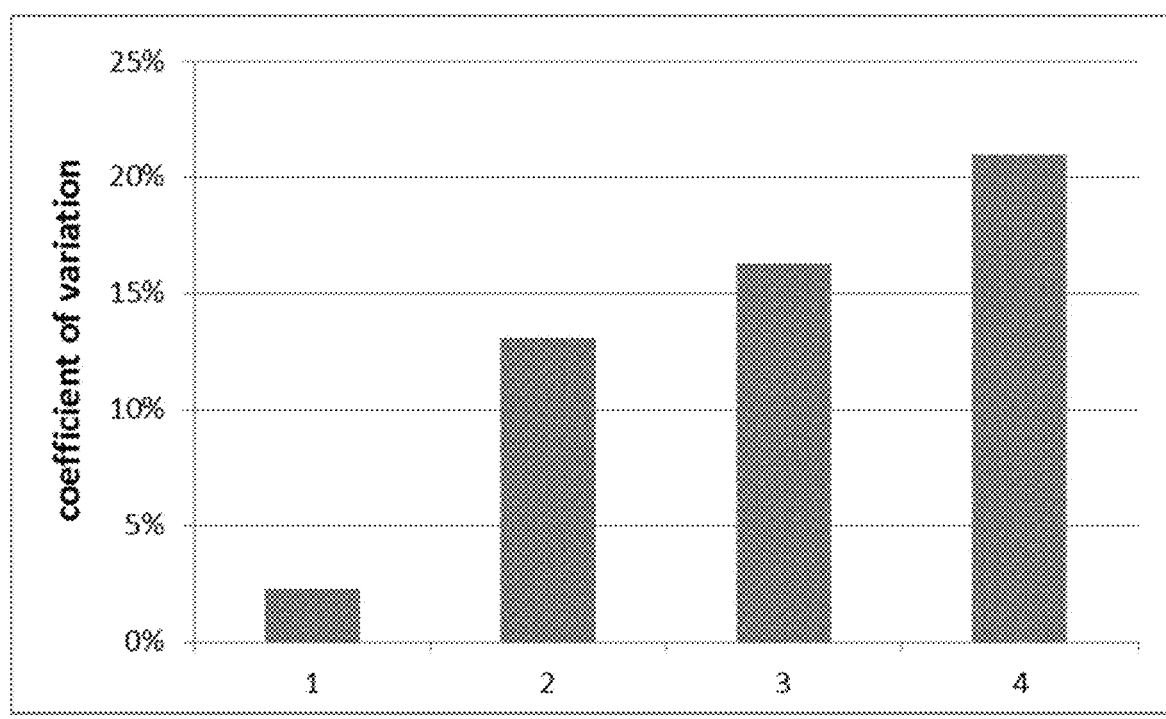
FIG. 3 Comparison of different method setups with respect to the coefficients of variation. 1) Method as described herein; 2) Method as described herein lacking the centrifugation step; 3) Method as described herein lacking the centrifugation step and lacking the step of stopping the reaction by addition on IAA; 4) Method as described herein lacking the centrifugation step and lacking the step of stopping the reaction by addition on IAA and lacking the dilution step FIG. 4 Comparison of the method as reported herein (1) with the methods as described in Matsumoto et al. ((2) GOD(GOx) activity assay; (3) HRP activity assay) with respect to activity, standard deviation and background.

Results: (see FIG. 3)

|  | Setup 1 | Setup 2 | Setup 3 | Setup 4 |
| --- | --- | --- | --- | --- |
| Run A | 0.3161 | 0.368 | 0.4539 | 0.5737 |
| Run B | 0.3318 | 0.3024 | 0.3281 | 0.7783 |
| Run C | 0.33 | 0.2856 | 0.2822 | 0.6901 |
| Run D | 0.329 | 0.2967 | 0.3915 | 0.5211 |
| Run E | 0.3272 | 0.3616 | 0.3901 | 0.8019 |
| Run F | 0.3152 | 0.3872 | 0.4083 | 0.4863 |
| mean value | 0.3249 | 0.3336 | 0.3757 | 0.6419 |
| standard deviation | 0.0073 | 0.0436 | 0.0611 | 0.1342 |
| % variation | 2% | 13% | 16% | 21% |

EXAMPLE 4

Measuring Sortase Activity, Standard Deviation and Background Signal Compared to Methods in Matsumoto et al. (2012)

The experiments were performed like described in example 2. The substrate concentrations were chosen analog the publication of Matsumoto et al. (2011 and 2012) (5 µM Sort-tag LPKTG, 20 µM Nucleophile GGG-Biotin). The temperature, time of incubation and the enzyme concentration were chosen analog to Matsumoto et al. (2012) (2.1 µM SrtA, 25 C° and 30 min).

Data for GOx (termed GOD in Matsumoto et al.) activity and HRP activity was taken from Matsumoto et al. (2012).

Results for method as described herein (example 2):

|  | Activity | Background |
| --- | --- | --- |
| Run A | 0.3161 | −0.0002061 |
| Run B | 0.3318 | 0.0004713 |
| Run C | 0.33 | −0.0002649 |
| Run D | 0.329 | −4.93E−17 |
| Run E | 0.3272 | 0.0006773 |
| Run F | 0.3152 | 0.0002065 |
| Mean value | 0.3249 | 0.0001473 |
| standard deviation | 0.0073 | 0.0003757 |

Figure 4:
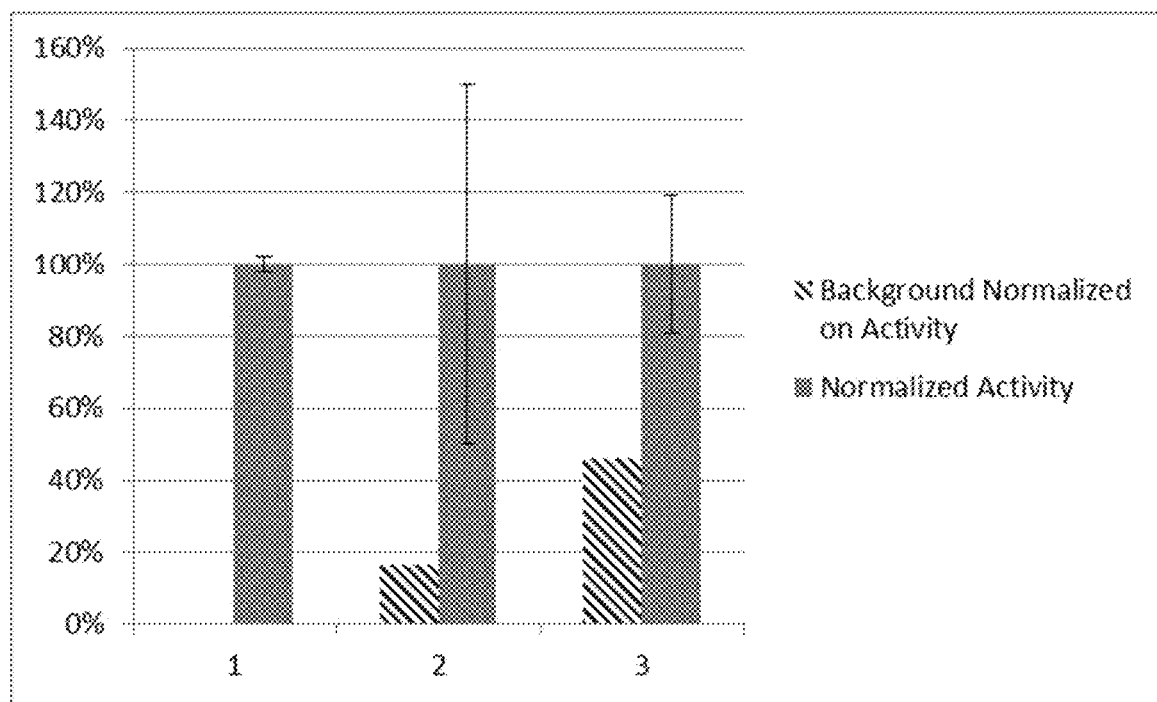

Results compared to methods of Matsumoto et al. (see FIG. 4)

|  | Method as reported herein | GOx (Matsumoto) | HRP (Matsumoto) |
| --- | --- | --- | --- |
| Activity | 0.3249 | 1200 | 0.26 |
| standard deviation | 0.0073 | 600 | 0.05 |
| Background | 3.6969E−05 | 200 | 0.12 |
| Normalized Activity | 100% | 100% | 100% |
| standard deviation | 2% | 50% | 19% |
| Background Normalized on Activity | 0% | 17% | 46% |

---

The invention claimed is:

1. A method for the detection of a bond forming enzyme in a sample, comprising the following steps:
   a) incubating the sample in a solution with a first substrate comprising an immobilization tag and a second substrate comprising a detectable label, whereby in the presence of a bond forming enzyme in the sample a conjugate comprising the immobilization tag and the detectable label is formed,
   b) centrifuging the solution from step a) and collecting a supernatant,
   c) immobilizing the conjugate in the supernatant of step b) using the immobilization tag to a solid phase, and
   d) detecting the immobilized conjugate using the detectable label, thereby detecting the bond forming enzyme in the sample.

2. The method according to claim 1, wherein after the incubation of step a) additionally the sample is diluted between 10 times and 30 times.

3. The method according to claim 1, wherein the first substrate comprising an immobilization tag comprises a first bond forming enzyme recognition motif and the second substrate comprising a detectable label comprises a second bond forming enzyme recognition motif.

4. The method according to claim 2, wherein the first substrate comprising an immobilization tag comprises a first bond forming enzyme recognition motif and the second substrate comprising a detectable label comprises a second bond forming enzyme recognition motif.

5. The method according to claim 3, wherein the first bond forming enzyme recognition motif is a first sortase recognition motif and the second bond forming enzyme recognition motif is a second sortase recognition motif.

6. The method according to claim 4, wherein the first bond forming enzyme recognition motif is a first sortase recognition motif and the second bond forming enzyme recognition motif is a second sortase recognition motif.

7. The method according to claim 5, wherein
   a) the first sortase recognition motif comprises an LPXTG motif (SEQ ID NO: 01), wherein X represents any amino acid and the second sortase recognition motif comprises an oligo-glycine or oligo-alanine motif or
   b) the second sortase recognition motif comprises an LPXTG motif (SEQ ID NO: 01), wherein X represents any amino acid and the first sortase recognition motif comprises an oligo-glycine or oligo-alanine motif.

8. The method according to claim 6, wherein
   a) the first sortase recognition motif comprises an LPXTG motif (SEQ ID NO: 01), wherein X represents any amino acid and the second sortase recognition motif comprises an oligo-glycine or oligo-alanine motif or
   b) the second sortase recognition motif comprises an LPXTG motif (SEQ ID NO: 01), wherein X represents any amino acid and the first sortase recognition motif comprises an oligo-glycine or oligo-alanine motif.

9. The method according to claim 1, wherein the detectable label is an enzyme.

10. The method according to claim 1, wherein the immobilization tag is a first member of a specific binding pair and the solid phase is conjugated to the second member of the specific binding pair.

11. The method according to claim 3, wherein the immobilization tag is a first member of a specific binding pair and the solid phase is conjugated to the second member of the specific binding pair.

12. The method according to claim 4, wherein the immobilization tag is a first member of a specific binding pair and the solid phase is conjugated to the second member of the specific binding pair.

13. The method according to claim 1, wherein the immobilization tag is biotin and the solid phase is conjugated to streptavidin or avidin.

14. The method according to claim 10, wherein the immobilization tag is biotin and the solid phase is conjugated to streptavidin or avidin.

15. The method according to claim 11, wherein the immobilization tag is biotin and the solid phase is conjugated to streptavidin or avidin.

16. The method according to claim 12, wherein the immobilization tag is biotin and the solid phase is conjugated to streptavidin or avidin.

17. The method according to claim 13, wherein the solid phase is a multiwell plate or a bead.

18. The method according to claim 14, wherein the solid phase is a multiwell plate or a bead.

19. The method according to claim 15, wherein the solid phase is a multiwell plate or a bead.

20. The method according to claim 16, wherein the solid phase is a multiwell plate or a bead.

21. The method according to claim 1, wherein after the incubation of step a) the sample is diluted with a solution comprising iodacetamide (IAA).

22. The method according to claim 1, wherein the sample is centrifuged between 5 min and 15 min and at between 2500×g to 7500×g.

23. The method according to claim 2, wherein the sample is centrifuge between 5 min and 15 min and at between 2500×g to 7500×g.

24. The method according to claim 21, wherein the sample is centrifuged between 5 min and 15 min and at between 2500×g to 7500×g.

25. The method according to claim 1, wherein after the immobilization of step c) additionally the sample is washed at least 3 times.

26. The method according to claim 21, wherein after the immobilization of step c) additionally the sample is washed at least 3 times.

27. The method according to claim 22, wherein after the immobilization of step c) additionally the sample is washed at least 3 times.

28. The method according to claim 23, wherein after the immobilization of step c) additionally the sample is washed at least 3 times.

29. The method according to claim 24, wherein after the immobilization of step c) additionally the sample is washed at least 3 times.

30. A method for selecting a bond forming enzyme from a multitude of bond forming enzymes comprising the steps of: a) providing at least two bond forming enzymes, b) performing the method of claim 1 with the at least two bond forming enzymes, and c) selecting a bond forming enzyme detected in step b).

31. The method according to claim 30, wherein the bond forming enzymes with the highest activity is selected.

32. The method according to claim 30, wherein the bond forming enzyme is a sortase.

* * * * *

SEQUENCE LISTING

```
<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      sortase motif
<220> FEATURE:
<221> NAME/KEY: MOD_RES
<222> LOCATION: (3)..(3)
<223> OTHER INFORMATION: Any amino acid

<400> SEQUENCE: 1

Leu Pro Xaa Thr Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      sortase motif
```

```
<220> FEATURE:
<221> NAME/KEY: MOD_RES
<222> LOCATION: (3)..(3)
<223> OTHER INFORMATION: Any amino acid

<400> SEQUENCE: 2

Leu Pro Xaa Thr Ala
1               5

<210> SEQ ID NO 3
<211> LENGTH: 3
<212> TYPE: PRT
<213> ORGANISM: Artificial Sequence
<220> FEATURE:
<223> OTHER INFORMATION: Description of Artificial Sequence: Synthetic
      oligoglycine

<400> SEQUENCE: 3

Gly Gly Gly
1

<210> SEQ ID NO 4
<211> LENGTH: 3
<212> TYPE: PRT
<213> ORGANISM: Artificial Sequence
<220> FEATURE:
<223> OTHER INFORMATION: Description of Artificial Sequence: Synthetic
      oligoalanine

<400> SEQUENCE: 4

Ala Ala Ala
1

<210> SEQ ID NO 5
<211> LENGTH: 2
<212> TYPE: PRT
<213> ORGANISM: Artificial Sequence
<220> FEATURE:
<223> OTHER INFORMATION: Description of Artificial Sequence: Synthetic
      oligoglycine
<220> FEATURE:
<221> NAME/KEY: MOD_RES
<222> LOCATION: (2)..(2)
<223> OTHER INFORMATION: Gly-biotin

<400> SEQUENCE: 5

Gly Gly
1

<210> SEQ ID NO 6
<211> LENGTH: 2
<212> TYPE: PRT
<213> ORGANISM: Artificial Sequence
<220> FEATURE:
<223> OTHER INFORMATION: Description of Artificial Sequence: Synthetic
      oligoglycine
<220> FEATURE:
<221> NAME/KEY: MOD_RES
<222> LOCATION: (2)..(2)
<223> OTHER INFORMATION: Gly-streptavidin

<400> SEQUENCE: 6

Gly Gly
1

<210> SEQ ID NO 7
<211> LENGTH: 2
<212> TYPE: PRT
<213> ORGANISM: Artificial Sequence
```

```
<220> FEATURE:
<223> OTHER INFORMATION: Description of Artificial Sequence: Synthetic
      oligoalanine
<220> FEATURE:
<221> NAME/KEY: MOD_RES
<222> LOCATION: (2)..(2)
<223> OTHER INFORMATION: Ala-biotin

<400> SEQUENCE: 7

Ala Ala
1

<210> SEQ ID NO 8
<211> LENGTH: 2
<212> TYPE: PRT
<213> ORGANISM: Artificial Sequence
<220> FEATURE:
<223> OTHER INFORMATION: Description of Artificial Sequence: Synthetic
      oligoalanine
<220> FEATURE:
<221> NAME/KEY: MOD_RES
<222> LOCATION: (2)..(2)
<223> OTHER INFORMATION: Ala-streptavidin

<400> SEQUENCE: 8

Ala Ala
1
```